(12) United States Patent
Smith

(10) Patent No.: US 6,761,702 B2
(45) Date of Patent: Jul. 13, 2004

(54) DEVICE AND METHOD FOR COLONIC LAVAGE

(75) Inventor: Alan Smith, Bromley (GB)

(73) Assignee: Intermark Medical Innovations LTD, Bromley (GB)

( * ) Notice: Subject to any disclaimer, the term of this patent is extended or adjusted under 35 U.S.C. 154(b) by 131 days.

(21) Appl. No.: 10/145,908

(22) Filed: May 16, 2002

(65) Prior Publication Data

US 2002/0188244 A1 Dec. 12, 2002

(30) Foreign Application Priority Data

May 31, 2001 (GB) .............................................. 0113145

(51) Int. Cl.$^7$ ................................................. A61M 1/00
(52) U.S. Cl. .......................................... 604/35; 604/27
(58) Field of Search .................. 604/27, 28, 39–45, 604/54, 35, 96.01, 275, 276, 278, 279

(56) References Cited

U.S. PATENT DOCUMENTS

| | | | | |
|---|---|---|---|---|
| 3,735,751 A | * | 5/1973 | Katz | 600/563 |
| 3,771,522 A | | 11/1973 | Waysilk et al. | |
| 3,823,714 A | * | 7/1974 | Waysilk et al. | 604/28 |
| 3,908,660 A | | 9/1975 | Kaplan et al. | |
| 4,519,385 A | * | 5/1985 | Atkinson et al. | 601/161 |
| 4,637,814 A | * | 1/1987 | Leiboff | 604/27 |
| 5,397,304 A | * | 3/1995 | Truckai | 604/528 |
| 5,443,445 A | | 8/1995 | Peters et al. | |
| 5,860,916 A | * | 1/1999 | Pylant | 600/208 |

FOREIGN PATENT DOCUMENTS

| | | |
|---|---|---|
| WO | WO 92/04059 | 3/1992 |
| WO | WO 01/32239 | 5/2001 |

OTHER PUBLICATIONS

Hepworth et al., "A New Safe, Simple and Swift Retrograde Method for on Table Lavage", Gut 1999: 44 (suppl. 1)A134: TH533.

* cited by examiner

*Primary Examiner*—Manuel Mendez
(74) *Attorney, Agent, or Firm*—Stites & Harbison PLLC; Douglas E. Jackson

(57) ABSTRACT

A device for colonic lavage has a tubular body (10) having a forward portion (12) and a rearward portion (14). An opening (16) is provided at the front end of the forward portion (12). A side tube (18) includes an outlet (20), thereby defining a continuous passage (22) from the opening (16) to the outlet (20). A port (24) is located at the other end of the tubular body (10) and incorporates a seal (28) having a free internal dimension (I) less than the minimum cross-sectional dimension (M) of the passage (22). The junction (17) between the forward portion and the side tube (18) is flexible. A discharge tube (32) extends from the outlet (20) to a sealable container. In use, the forward portion (12) of the tubular body (10) is inserted into the bowel of a patient. A hose (26) is inserted into the port (24) to extend through the tubular body (10) and through the opening (16) into the colon of the patient. Irrigation fluid is passed through the hose (26) to cleanse obstructed fecal matter from the colon. Cleansed fecal matter is discharged from the tubular body through the outlet (20) and the discharge tube to the container (40). The hose (26) is advanced through the device further into the colon as obstructed fecal matter is cleansed therefrom.

17 Claims, 2 Drawing Sheets

DEVICE AND METHOD FOR COLONIC LAVAGE

FIELD OF THE INVENTION

This invention relates to a device for colonic lavage, and to a method for using such a device, particularly for on-table retrograde lavage.

BACKGROUND TO THE INVENTION

In emergency surgery a clean, well prepared bowel is required for safe colonic resection and anastomosis. Both antegrade and retrograde on-table lavage methods are known. Antegrade methods are more often used and require a further incision in the bowel to place a catheter to administer irrigation fluid.

U.S. Pat. No. 5,443,445 (Peters et al./Clinical Product Development Limited) describes an intra-operative colon irrigation system which includes a device having a tubular body with a forward end formed by a dome-shaped nozzle to prevent intussusception of the bowel, and a side tube including an outlet for the discharge of fecal matter from the device. A port is located at the other end of the tubular body, for the insertion of an ultrasonic device or for the injection of water or air under pressure.

However, retrograde methods would be preferred in that no additional incision of the bowel is required.

Hepworth et al., in Gut 1999; 44 (suppl.1), A134: TH533, have proposed a retrograde procedure for on-table lavage which comprises advancing a jet of irrigation fluid through the bowel as the lavage process proceeds.

A known device for such a retrograde lavage method comprises a rigid Y-connector to which three flexible tubes are connected. One tube is inserted in the bowel and another carries irrigation fluid, while the third leads to a container for the irrigated fecal material. This device has not proved ideal. In particular, the rigid Y-tube easily becomes blocked with fecal material and it is difficult to advance the irrigation fluid tube through the Y-connector as the lavage process proceeds. Furthermore, the "Y" configuration of the connector prevents the insertion of a colonoscope through the device, a colonoscope being used after lavage to check the condition of the bowel.

SUMMARY OF THE INVENTION

It is an object of the present invention to provide a more suitable device for carrying out the process suggested by Hepworth et al. and to provide a method of using such a device.

Generally, this invention provides a device for colonic lavage, comprising a tubular body having a forward portion and a rearward portion, an opening at the front end of the forward portion for insertion into the bowel of a patient, a side tube including an outlet for the discharge of fecal matter from the device, thereby defining a continuous passage from the opening to the outlet, and a port located at the other end of the tubular body, and incorporating sealing means to enable the insertion of a hose into the device, the sealing means having a free internal dimension less than the minimum cross-sectional dimension of the passage, and wherein at least that portion of the tubular body which constitutes a junction between the forward portion and the side tube is flexible.

The invention also generally provides a method for colonic lavage by use of a device comprising a tubular body having a forward portion and a rearward portion, an opening at the front end of the forward portion for insertion into the bowel of a patient, a side tube including an outlet for the discharge of fecal matter from the device, thereby defining a continuous passage from the opening to the outlet, and a port located at the other end of the tubular body, the method comprising inserting the forward portion of the tubular body into the bowel of a patient, inserting a hose into the port to extend through the tubular body and through the opening into the colon of the patient, passing irrigation fluid through the hose to cleanse obstructed fecal matter from the colon, allowing cleansed fecal matter to be discharged from the tubular body through the outlet, and advancing the hose through the device further into the colon as obstructed fecal matter is cleansed therefrom.

The opening in the tubular body is preferably unobstructed, so as to allow cleansed fecal matter to pass freely into the device through the opening. This is in contrast to the device described in U.S. Pat. No. 5,443,445, referred to above, where the opening at the forward end of the tubular body is intentionally obstructed by a dome-shaped nozzle.

The port is preferably in straight line relationship with the opening in the tubular body. This enables the hose to be more easily advanced through the device in use, without any bends or turns, and also enables alternative components, such as a colonoscope, to be inserted through the device into the colon of the patient.

At least that portion of the tubular body which constitutes a junction between the forward portion and the side tube is flexible e.g. is formed of flexible material, so as to enable the operator to dislodge any blockage which may occur at this point, as a consequence of the build-up of fecal material in this region, by manipulating the flexible portions of the device. Most preferably the whole device is made of flexible material.

According to a preferred aspect of the invention, a discharge tube extends from the outlet to a sealable, preferably flexible, container. The discharge tube preferably has a concertina configuration to enable any blockage within the discharge tube to be dislodged by extending and contracting blocked section of the discharge tube. The discharge tube is preferably releasably connected to the container to enable the container to be easily exchanged when full. The construction of the container can be chosen such that when full, it is of a size and weight which can be easily disposed of safely.

The side tube is preferably shaped to constitute a hand grip, to ease control of the device by the operator.

The tubular body is preferably formed of a medical grade material such as PVC or silicone and may be manufactured by blow molding or dip molding. The forward and rearward portions of the tubular body and the side arm are usefully formed as an integral entity.

The sealing means is preferably an annular seal associated with the port. The seal may be formed of medical grade material such as PVC and secured to the tubular body by bonding e.g. with a medical grade bonding agent such as cyclohexanone.

The device according to the invention can be used together with a hose which is a close fit in the sealing means, the hose having a length exceeding the distance from the port to the opening, ideally having a length which is considerably longer than the device to enable the hose to be advanced as required through the colon of the patient, while continuing to be connected to the irrigation fluid source. The hose may be advanced through the device by hand. To assist the advance of the hose through the sealing means it is preferred to form the hose and the sealing means from low-friction material, or to coat these members with such a material.

The irrigation fluid will normally be a liquid, although the device is suitable for use with compressed air, or a mixture of air and liquid. A suitable liquid is a saline solution.

BRIEF DESCRIPTION OF THE DRAWING

The invention will be described in further detail, purely by way of example, with reference to the accompanying drawings, in which.

DETAILED DESCRIPTION

Figure 1:
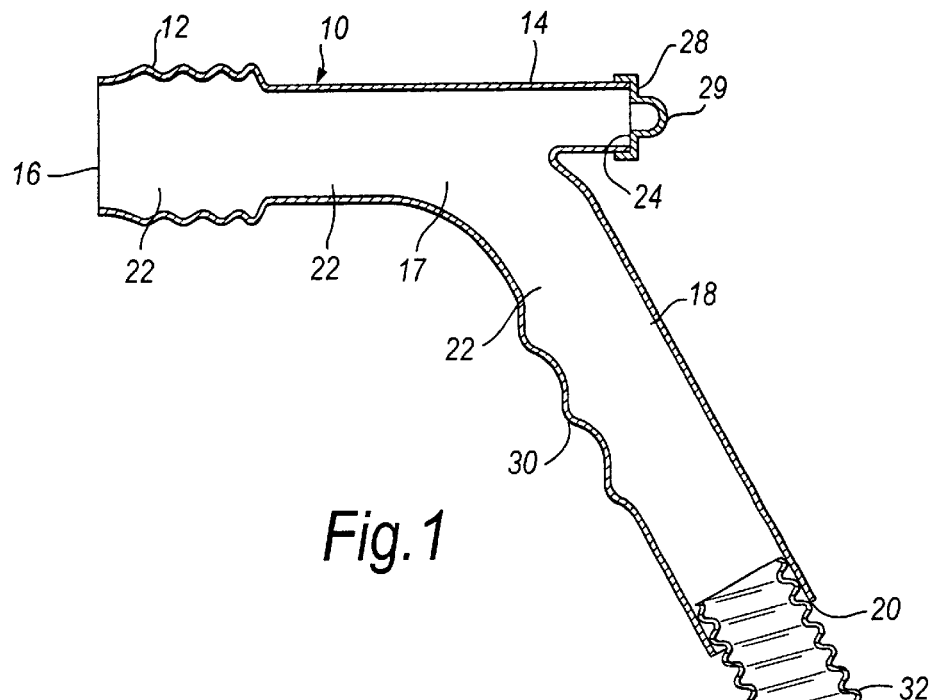
FIG. 1 is a longitudinal cross-sectional view of one embodiment of a colonic lavage device according to the invention.

The colonic lavage device shown in the drawings includes an integral tubular body 10 having a length of 180 mm formed by dip molding and having a corrugated forward portion 12 having a minimum internal diameter M of 32 mm and a cylindrical rearward portion 14. An unobstructed circular opening 16 is formed at the front end of the forward portion 12. The tubular body is formed of 80 Shore A medical grade PVC having a thickness of 2 to 3 mm.

The tubular body 10 includes a side tube 18 having a circular outlet 20, thereby defining a continuous passage 22 from the opening 16 to the outlet 20. The side tube is shaped to constitute a hand grip 30. A clear concertinaed discharge tube 32 extends from the outlet 20 to a sealable container 40.

The cylindrical rearward portion 14 of the tubular body 10 includes a port 24 of circular cross-section located at the end opposite to the opening 16, the port 24 having an internal diameter of 16 mm. An annular seal 28, formed of medical grade PVC and closed by a nipple 29 is bonded to the tubular body 10 by a medical grade adhesive and closes the port 24. The seal 28 has a free internal diameter (I) of 7 mm.

In use, the forward portion 12 of the tubular body 10 is inserted into the proximal bowel of a patient, e.g. following resection of a tumor. The corrugated construction of the forward portion 12 of the tubular body 10 enables the bowel to be secured thereto in a leak-free manner. e.g. by the use of straps.

Figure 2:
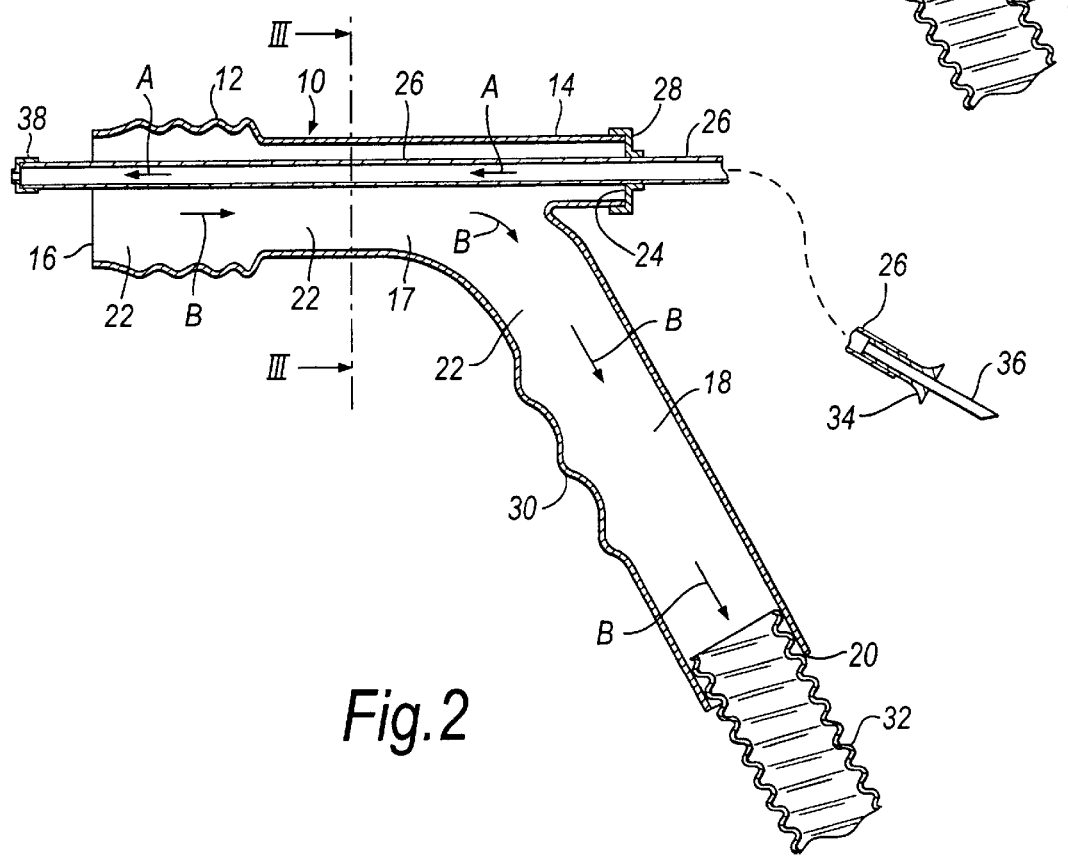
FIG. 2 is a cross-sectional view of the colonic lavage device shown in FIG. 1, together with a hose in the in-use position.
Figure 3:
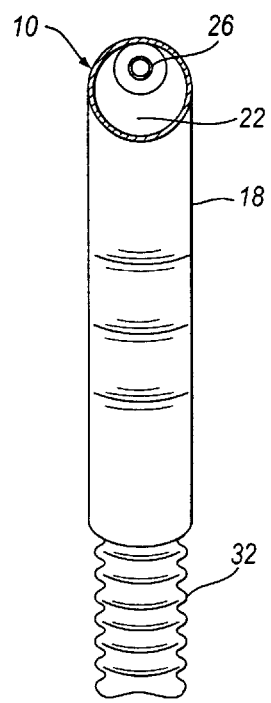
FIG. 3 is a lateral cross-section, taken on the line III—III in FIG. 2.

As shown in FIGS. 2 and 3, after cutting off the nipple 29 and applying a lubricant such as KY-jelly (Trade Mark), ex. Johnson & Johnson, to the seal 28, a medical grade PVC hose 26, having an external diameter of 8 mm and a length of 3.5 m or more, is inserted through the seal 28 to extend through the tubular body 10 and the opening 16 into the colon of the patient. The hose 26 is a close fit in the under-sized annular seal 28. The hose 26 carries a cap 38 at its forward end to increase nozzle pressure and protect the inside of the colon, while at its other end it carries an insert 34 incorporating a spike 36, for connection to a standard saline supply bag. Saline solution is passed under gravity through the hose 26 as shown by the arrows A, to cleanse obstructed fecal matter from the colon. Although not shown in the drawings, a clamp or other controllable closing device may be provided at a convenient position along the length of the hose 26, upstream of the device, to enable the operator to control the rate of flow of saline into the colon.

Cleansed fecal matter returns to the tubular body 10 to be discharged through the outlet 20, as shown by the arrows B. The concertinaed construction of the discharge tube 32 enables any blockage therein to be easily dislodged by extending and contracting the blocked sections of this tube. The hose 26 is advanced by hand through the device further into the colon as obstructed fecal matter is cleansed therefrom. The clear construction of the discharge tube 32 enables the operator to see when the returning liquid is running clean, indicating that the lavage process is complete.

Figure 4:
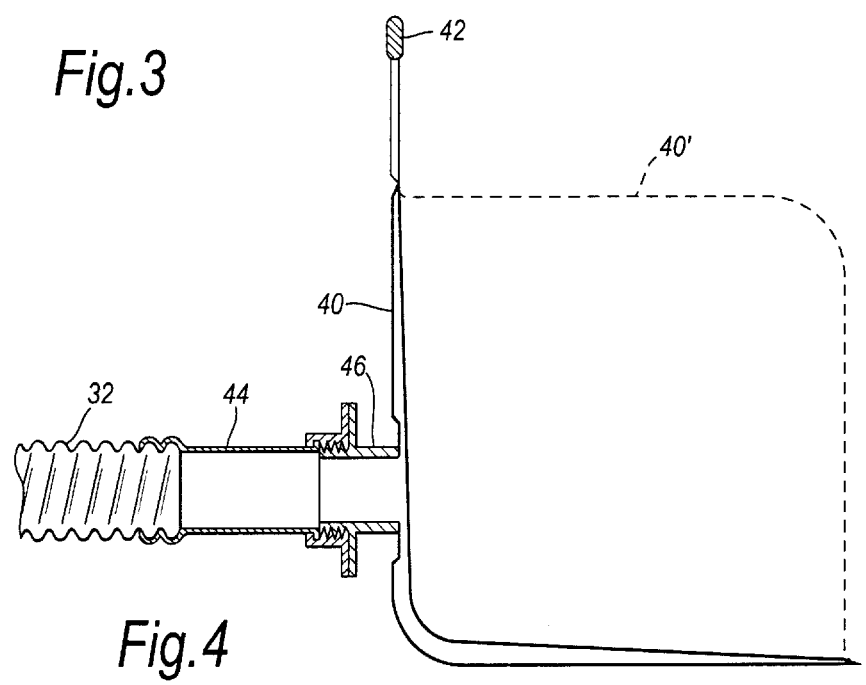
FIG. 4 is a cross-section of a container, to which the discharge tube of the device shown in FIGS. 1 to 3 is attached.

As shown in FIG. 4, the container 40 is formed of flexible polyethylene and is as to be able to adopt the collapsed configuration shown in heavy lines, while being expandable to the configuration shown in broken lines 40'. In the expanded condition, the container 40 has a volume of about 10 l. The container is provided with a carrying handle 42. The concertinaed discharge tube 32 carries an end piece 44, which can be screwed onto a threaded spigot 46 of the container 40. When the container 40 is full, the discharge tube 32 can be removed therefrom and replaced by a closure cap.

I claim:

1. A device for colonic lavage, comprising
   a tubular body having a forward portion and a rearward portion,
   an opening at the front end of said forward portion for insertion into the bowel of a patient,
   a side tube including an outlet for the discharge of fecal matter from the device, thereby defining a continuous passage from said opening to said outlet, and
   a port located at the other end of the tubular body and incorporating an annular seal bonded to said tubular body to enable the insertion of a hose into the device, said annular seal having a free internal dimension less than the minimum cross-sectional dimension of said passage and wherein at least that portion of said tubular body which constitutes a junction between said forward portion and said side tube is flexible.

2. The device of claim 1, wherein said opening is unobstructed.

3. The device of claim 1, wherein said port is in straight line relationship with said opening.

4. The device of claim 1, together with a hose which is a close fit in said sealing means, said hose having a length exceeding the distance from said port to said opening.

5. The device of claim 4, wherein said hose has a nozzle at its forward end.

6. The device of claim 1, wherein said side tube is shaped to constitute a hand grip.

7. The device of claim 1, together with a discharge tube extending from said outlet to a container.

8. The device of claim 1, wherein said annular seal is closed by a nipple.

9. The device of claim 1, wherein said forward portion of said tubular body is corrugated.

10. A device for colonic lavage, comprising
    a tubular body having a forward portion and a rearward portion,
    an opening at the front end of said forward portion for insertion into the bowel of a patient,
    a side tube including an outlet for the discharge of fecal matter from the device, thereby defining a continuous passage from said opening to said outlet, and a port located at the other end of the tubular body, together with a discharge tube extending from said outlet, a sealable container, including a threaded spigot onto which an end piece of the discharge tube is removably screwed, and a closure cap which is screwed onto said threaded spigot in place of said end piece to seal the container when the latter is full.

11. The device of claim 10, wherein said discharge tube has a concertina configuration.

12. A method for colonic lavage by use of a device comprising a tubular body having a forward portion and a rearward portion, an opening at the front end of said forward portion for insertion into the bowel of a patient, a side tube including an outlet for the discharge of fecal matter from the device, thereby defining a continuous passage from said opening to said outlet, and a port located at the other end of the tubular body, the method comprising inserting said forward portion of said tubular body into the bowel of a patient, inserting a hose into said port to extend through said tubular body and through said opening into the colon of said patient, the hose having a nozzle at the forward end thereof, passing irrigation fluid through said hose and said nozzle to cleanse obstructed fecal matter from said colon, allowing cleansed fecal matter to be discharged from said tubular body through said outlet, and advancing said hose through said device further into said colon as obstructed fecal matter is cleansed therefrom.

13. The method of claim 12, wherein any blockage within said device is dislodged by manipulating flexible portions of said device.

14. The method of claim 12, wherein a discharge tube of concertina configuration extends from said outlet to a container, and any blockage within said discharge tube is dislodged by extending and contracting the blocked section of said discharge tube.

15. The method of claim 12, wherein said port incorporates an annular seal bonded to said tubular body with said annular seal being closed by a nipple and having a free internal dimension less than the minimum cross-sectional dimension of said passage, wherein the inserting of said hose into said port step includes cuffing off said nipple and applying a lubricant to said seal.

16. The method of claim 15, wherein said port is in straight line relationship with said opening and further including the step of alternately inserting a colonoscope through the device into the colon of said patient to check the condition of the bowel.

17. The method of claim 12, wherein said forward portion of said tubular body is corrugated and said bowel is secured to said forward portion in a leak-free manner by the use of straps.

* * * * *